(12) United States Patent
Jikomes et al.

(10) Patent No.: US 11,972,469 B2
(45) Date of Patent: Apr. 30, 2024

(54) SYSTEM AND MACHINE-READABLE MEDIA FOR SELECTION OF REGULATED PRODUCTS

(71) Applicant: Leafly Holdings, Inc., Seattle, WA (US)

(72) Inventors: Nickolas Jikomes, Seattle, WA (US); Marc Brandon Hensley, Seattle, WA (US); Jason Makuch, Seattle, WA (US); Andrew MacRae, Seattle, WA (US); Nathan Lauer, Seattle, WA (US); Matthew Bollen, Seattle, WA (US); Stephanie Smith, Seattle, WA (US); Camille Lim, Seattle, WA (US); Michael Wityk, Seattle, WA (US); Adam Hilborn, New York, NY (US); Sam Starr, Sao Paulo (BR); Christian Ramsey, Seattle, WA (US); Renata Le Duartes, III, Seattle, WA (US); Santiago Seira, San Francisco, CA (US); Anna Zeng, Seattle, WA (US)

(73) Assignee: Leafly Holdings, Inc., Seattle, WA (US)

( * ) Notice: Subject to any disclaimer, the term of this patent is extended or adjusted under 35 U.S.C. 154(b) by 0 days.

(21) Appl. No.: 17/527,120

(22) Filed: Nov. 15, 2021

(65) Prior Publication Data

US 2022/0148067 A1 May 12, 2022

Related U.S. Application Data

(63) Continuation of application No. 16/228,197, filed on Dec. 20, 2018, now Pat. No. 11,205,210.

(51) Int. Cl.
*G06Q 30/00* (2023.01)
*G06Q 30/0601* (2023.01)
*G16H 40/63* (2018.01)

(52) U.S. Cl.
CPC ..... *G06Q 30/0631* (2013.01); *G06Q 30/0607* (2013.01); *G16H 40/63* (2018.01)

(58) Field of Classification Search
CPC . G06Q 30/0631; G06Q 30/0607; G16H 40/63
(Continued)

(56) References Cited

U.S. PATENT DOCUMENTS 7,308,423 B1 12/2007 Woodward et al.
7,668,761 B2 2/2010 Jenkins et al.
(Continued)

FOREIGN PATENT DOCUMENTS

WO 2017205853 A1 11/2017
WO 2020132370 A1 6/2020

OTHER PUBLICATIONS

Hacienda, Terry, This New App Will Change The Way You Buy Cannabis, 2018, May 9, The Fresh Toast, pp. 1-3. (Year: 2018).*
(Continued)

*Primary Examiner* — Jeffrey A. Smith
*Assistant Examiner* — Brittany E Bargeon
(74) *Attorney, Agent, or Firm* — Perkins Coie LLP

(57) ABSTRACT

A system for categorizing, visualizing, and recommending *Cannabis* products based on objective data of the chemical composition of products is described. This system allows *Cannabis* products to be visualized and compared based on their chemical composition, even by laypeople with little or no knowledge of the underlying objective data. A recommendation system is built upon this which can recommend products for consumption, including a user interface for receiving user input, which includes at least one of demographic data, desired level of psychoactivity, or prior experience with the product, a merchant interface for receiving merchant input, including at least one of general data descriptive of the regulated product, lab data descriptive of
(Continued)

the regulated products chemical composition, and user data descriptive of subjective effects of the regulated product on a user; and a decision engine making a recommendation of product according to correlation of the lab data with the user data.

14 Claims, 10 Drawing Sheets

(58) Field of Classification Search
USPC .......................................................... 705/26.7
See application file for complete search history.

(56) References Cited

U.S. PATENT DOCUMENTS

| | | | |
|---|---|---|---|
| 7,801,772 | B2 | 9/2010 | Woodward et al. |
| 8,010,411 | B2 | 8/2011 | Woodward et al. |
| 8,880,428 | B2 | 11/2014 | Woodward et al. |
| 9,519,934 | B2 | 12/2016 | Calman et al. |
| 9,916,560 | B2 | 3/2018 | Vasantham et al. |
| 10,319,475 | B1 | 6/2019 | Croan et al. |
| 11,205,210 | B2 | 12/2021 | Jikomes et al. |
| 11,341,559 | B2 | 5/2022 | Jikomes et al. |
| 11,367,519 | B1* | 6/2022 | Heldman ............... A61M 5/142 |
| 2002/0188527 | A1 | 12/2002 | Dillard et al. |
| 2007/0226120 | A1 | 9/2007 | Nanjundamoorthy |
| 2014/0189804 | A1 | 7/2014 | Lehmann et al. |
| 2014/0279221 | A1 | 9/2014 | Woodward et al. |
| 2015/0242420 | A1 | 8/2015 | Glover et al. |
| 2016/0207679 | A1 | 7/2016 | Jackson |
| 2016/0271252 | A1* | 9/2016 | Vangara ................... A61K 9/08 |
| 2016/0300289 | A1* | 10/2016 | Rose .................. G06Q 30/0607 |
| 2017/0067748 | A1 | 3/2017 | Glover et al. |
| 2017/0199168 | A1 | 7/2017 | Jackson et al. |
| 2018/0144390 | A1 | 5/2018 | Beckford |
| 2018/0158125 | A1* | 6/2018 | Perelman ............... G16H 70/40 |
| 2018/0284145 | A1 | 10/2018 | Giese et al. |
| 2018/0357701 | A1* | 12/2018 | Vu .......................... G16H 20/10 |
| 2020/0219167 | A1 | 7/2020 | Jikomes et al. |

OTHER PUBLICATIONS

Sexton M, Cuttler C, Finnell JS, Mischley LK, A cross-sectional survey of medical cannabis users: patterns of use and perceived efficacy, 2016, Cannabis and Cannabinoid Research 1:1, DOI: 10.1089/can.2016.0007, pp. 131-138. (Year: 2016).*

European Patent Office, Extended European Search Report, EP Patent Application 19899380.0, dated Jul. 29, 2022, 8 pages.

Cannabinder: Trust Your Cannabis [Online], What do the colors on the Cannastamp mean?[retrieved on Jun. 24, 2019]. Retrieved from the Internet: <URL: https://www.cannabinder.com/>, 5 pages.

Hacienda, Terry. "This New App Will Change The Way You Buy Cannabis," May 9, 2018, The Fresh Toast, pp. 1-3. (Year: 2018).

International Searching Authority: United States of America, International Search Report and Written Opinion, PCT Application No. PCT/US2019/067683; Applicant: Leafly Holdings, Inc., dated Apr. 16, 2020, 21 pages.

Rahn, Indica vs. Sative: "What's the difference between cannabis types?" Leafly, Sep. 20, 2018 [retrieved on Feb. 5, 2020]. Retrieved from the internet: <https://www.leafly.com/news/cannabis-101/sativa-indica-and-hybrid-differences-between- cannabis-types> 17p.

Washington State Liquor and Cannabis Board, Approved Shapes for Marijuana Infused Edibles, Published: Apr. 23, 2019, 1 page.

* cited by examiner

SYSTEM AND MACHINE-READABLE MEDIA FOR SELECTION OF REGULATED PRODUCTS

CROSS-REFERENCE TO RELATED APPLICATIONS

This application is a continuation of U.S. patent application Ser. No. 16/228,197 filed Dec. 20, 2018 (U.S. Pat. No. 11,205,210), which is incorporated herein by reference in its entirety.

BACKGROUND OF THE INVENTION

1. Field of the Invention

The invention disclosed herein relates to a system of categorization of a regulated product, and in particular, to an online system for recommending product exploration paths to users navigating through this product categorization schema and identifying locations for acquisition of such products.

2. Description of the Related Art

Retail purchasing by consumers has conventionally been done at a location, often referred to as a "brick and mortar" store. This has afforded access to salespeople that can share wisdom and provide advice about the various products and purchasing options. This is one of the added benefits of on-site shopping. Unfortunately, the advice is sometimes inaccurate, subjective, or a complete fabrication provided to drive sales. The consumer may, or may not, benefit from an onsite purchase that affords access to product expertise.

Increasingly, consumers are making purchases on-line. On-line shopping offers convenience, is expedient, and provides for discreet purchasing. Typically, on-line outlets (i.e., websites) offer consumer product reviews to compete with the on-site expertise of a brick-and-mortar outlet. Unfortunately, the reviews may be fake, subjective, or just inapplicable.

Consider, for example, the purchase of regulated products such as alcohol, tobacco or *Cannabis* products. When considering a potential purchase, the customer may wish to account for certain things such as taste, potency, potential biological effects or other such aspect. Often, such aspects may be governed, at least in part, by the physiology of the customer (i.e., also referred to as the "user"). Unfortunately, present purchasing outlets, whether on-site or on-line, do little to accommodate these purchasing decisions and rely heavily on anecdotal opinion or subjective data.

Thus, what are needed are methods and apparatus to accommodate the decision making process for purchase of regulated products. Preferably, the techniques account for collection and/or use of objective data in the purchasing decision.

SUMMARY OF THE INVENTION

In one embodiment, a categorization system for objectively categorizing a regulated product for consumption is disclosed, as well as a recommended decision tree which users can utilize in order to navigate products and product categories. For ease of reference, "products" and "product categories" as referred to throughout shall refer to *Cannabis* products and groups of products, respectively, which are hierarchically grouped based on objective data, though the present disclosure is envisioned for use in connection with products (e.g., alcohol, tobacco, etc.). Each product is either a "strain" of *Cannabis*, or else a product such as concentrated extract derived from one or more *Cannabis* strains. The system includes a user interface for displaying individual products using a novel form of visualization preferably generated based on lab data quantifying the chemical profile of each product, as well as for receiving and assessing user-specific data relating to such products.

This product classification schema based on objective data can also be used in combination with user feedback about the subjective effects of products within a category in order to power a recommendation system whereby users can be recommended products that will have similar or different effects based on whether they fall into the same or different product groupings, respectively.

In another embodiment, a computer program product comprising machine executable instructions stored on non-transitory machine readable media is provided. The instructions provide for recommending a regulated product for consumption by implementing a method of obtaining user input including at least one of personal data (e.g. sex, age, heartrate, blood pressure), preference data (e.g. saved history of "liking" or "not liking" a given product), and experience data (e.g. saved history of how a product made them feel); obtaining merchant input including at least one of general data descriptive of the regulated product, batch data descriptive of the regulated product and user data descriptive of felt effects of the regulated product on the user; and, making a recommendation of regulated product using a decision engine, the recommendation made according to correlation of the chemical data obtained from testing laboratories (which is used to categorize and visualize individual products) with the preference data obtained from user inputs.

BRIEF DESCRIPTION OF THE DRAWINGS

The features and advantages of the invention disclosed herein are apparent from the following description taken in conjunction with the accompanying drawings in which.

DETAILED DESCRIPTION OF THE INVENTION

Figure 1:
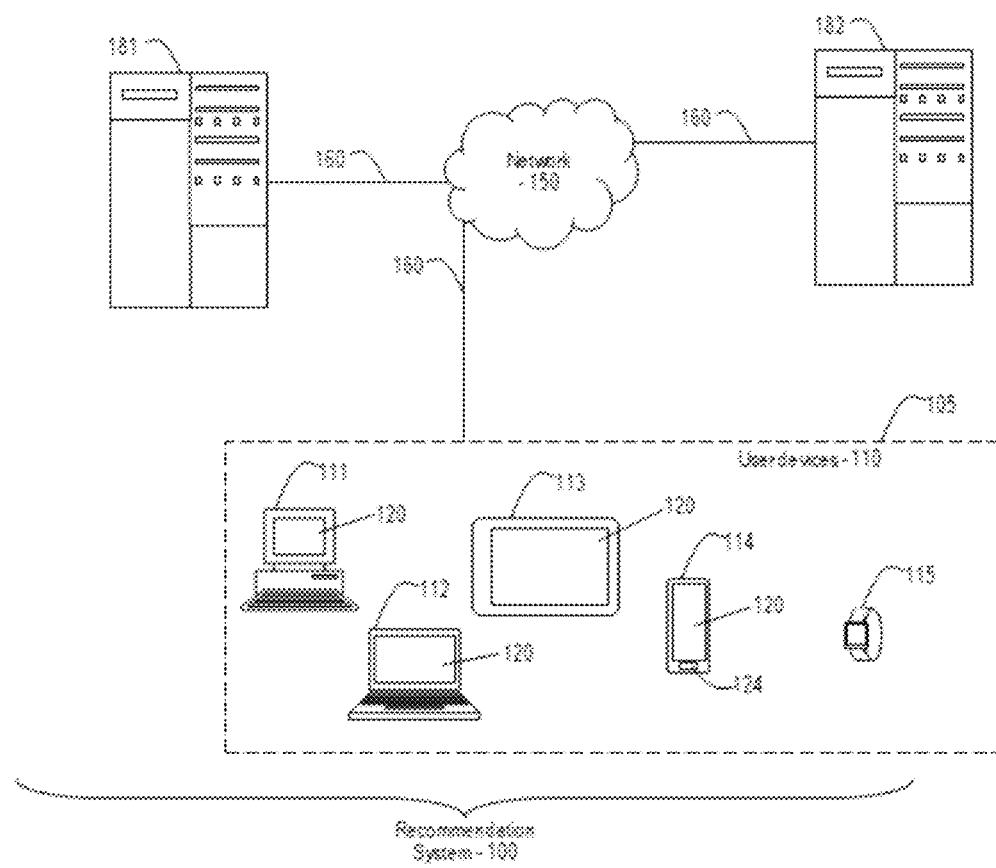
FIG. 1 is an schematic diagram depicting a recommendation system.

Disclosed herein are methods and apparatus for categorizing and recommending a product for purchase from a selection of products. For purposes of simplicity, the remainder of the disclosure sets forth the embodiment regarding *Cannabis*, though the disclosure is in no way limiting and any other product—regulated or unregulated—could form the basis for the categorization and recommendation of the products using the methods disclosed herein. However, this is not limiting and merely illustrative of the technology disclosed herein. There is no requirement that the products be subject to any particular regulation, unless such requirement is expressly stated herein.

The product visualizations and hierarchy of product groups described herein are preferably determined by objective data comprised of measurements of two major classes of chemical constituents found in *Cannabis*: cannabinoids and terpenes. Products are initially classified into one of three major groups defined by the ratio of the two principal cannabinoids found in *Cannabis* products, THC and CBD. The ratio of Total THC to Total CBD allows each product to be discretely placed into one of three groups in the highest level of the classification hierarchy: "THC-dominant," "CBD-dominant," or "Balanced THC/CBD." Products assigned to one of these three groups can be further grouped into separate groups nested within these primary groups if they have sufficiently high levels of another, less common cannabinoid. For example, a "THC-dominant" product may be further distinguished as "THC-dominant+THCV," indicating that it also contains relatively high levels of another cannabinoid. After this phase of classification based on cannabinoid, products are further grouped based on measurements of the second class of chemical compounds known as terpenes.

The second phase of the classification hierarchy assigns a product to a further group nested within the larger group assignment defined above. This group assignment is preferably determined by the "dominant" terpene found in the product, i.e. the terpene present at the highest concentration for that product type. *Cannabis* products within each of these dominant terpene subgroups are grouped further, at the next level of the hierarchy, based on the number and rank-order of terpene compounds present in that product. For example, two *Cannabis* product types nested within a single dominant terpene group, which is itself nested within a higher-level cannabinoid-based grouping, may be distinguished by having a different number or rank-order of secondary, tertiary, or quaternary terpenes.

These hierarchically-defined *Cannabis* product groupings are preferably determined at the highest level based on the major constituents commonly found in *Cannabis* known to cause or modulate the psychoactive effects of these products (principal cannabinoids such as THC and CBD) and at the lower levels by compounds thought or known to directly impact the flavor and smell, as well as potentially modulate the psychoactive effects, of *Cannabis* products (terpenes). Thus, products found within the same sub-groups will tend to have similar aromas and likely similar effects to other products within the same group. Products in different subgroups will tend to have different flavor and aroma profiles and different subjective effects (all other things being equal), especially when products fall into different high-level groups. Other hierarchical categorizations are also envisioned.

A novel visual design logic is also used to visualize individual products (e.g. individual *Cannabis* strains). The visualization for each strain is based on objective lab data consisting of measurements of the cannabinoid and terpene profile of that strain or product. "Strains" here refers to common *Cannabis* industry product labels (e.g. "Blue Dream") given to *Cannabis* products. Multiple product lines made by distinct producer-processors can be given the same strain name label. Lab data comprised of chemical profiles is obtained across multiple product lines with the same strain name label, and data are aggregated and cleaned, and a composite chemical profile is constructed for that strain. In addition, the same visualization can be applied to individual producer-processors' products, allowing similarities or differences in specific product lines to be visually discerned or compared to the composite visualization of all products with the same strain name.

Figure 5:
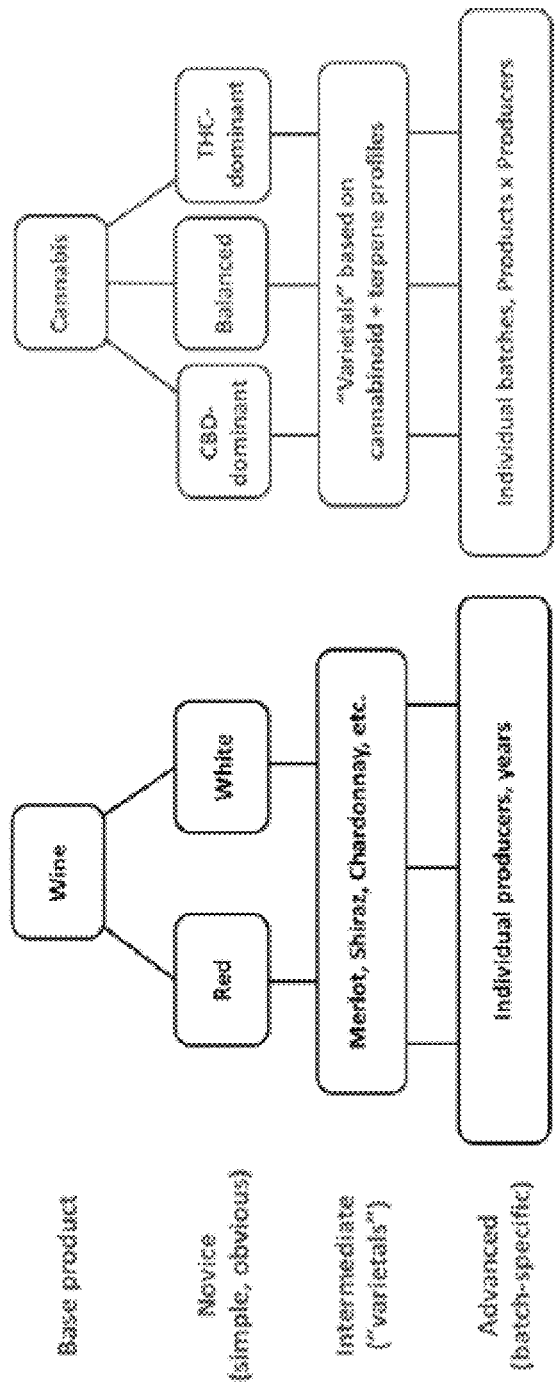
FIG. 5 is a sample decision tree represented by the present invention.

As seen in FIG. 5, strains of *Cannabis* product can be classified and sub-classified in the same manner as wine, for example. Just as a wine can be categorized into white wine or red wine, and then further into the type of wine and the vintage, *Cannabis* product can be categorized at many levels by its components, its effects, and its "vintage".

Figure 6:
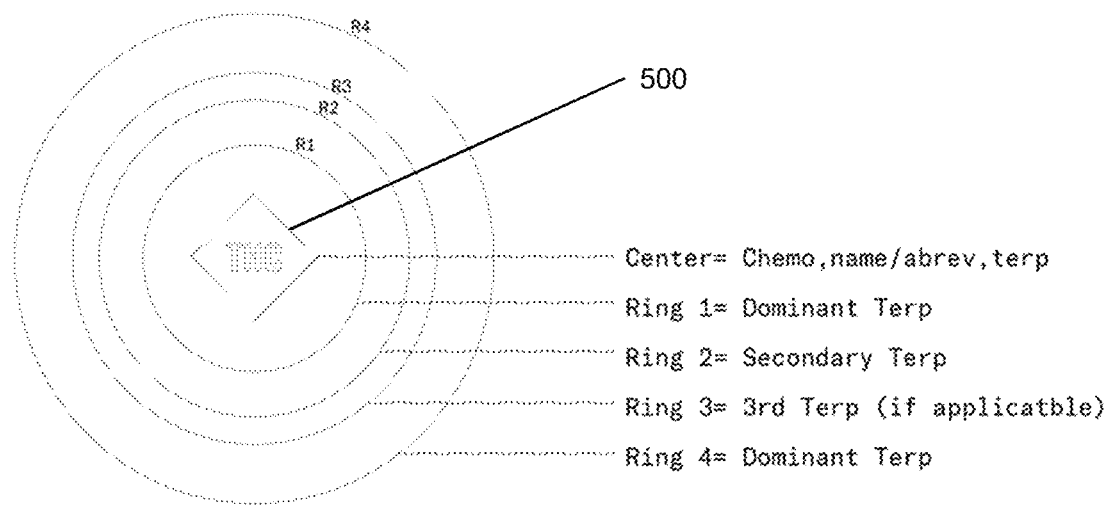
FIG. 6 is an example visualization logic utilized by the present invention.
Figure 7:
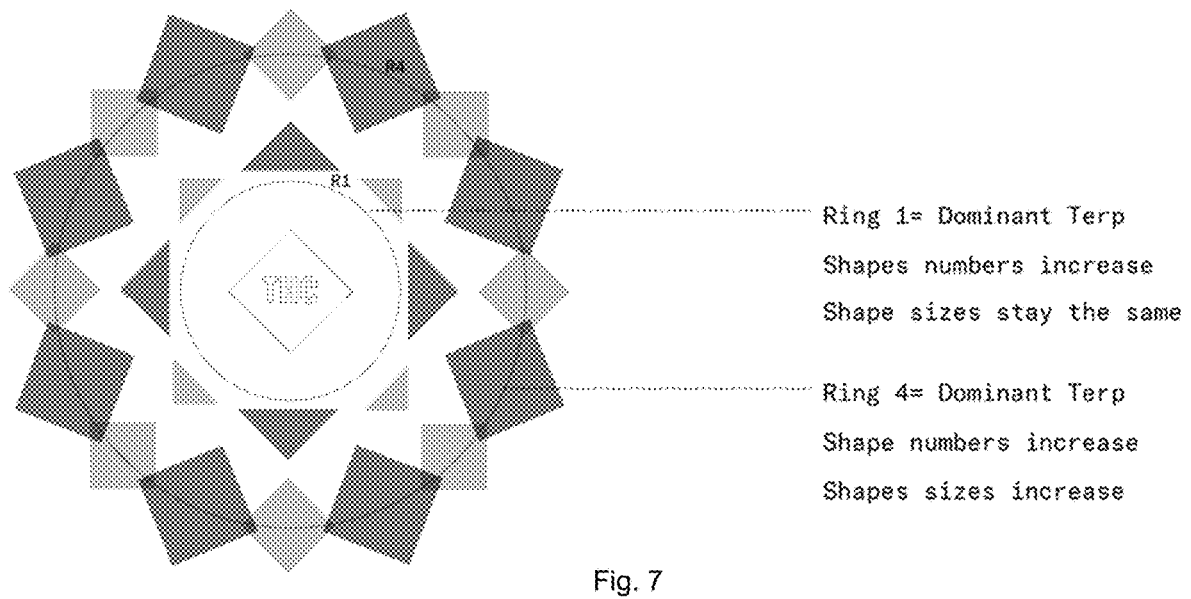
FIG. 7 is a further detailed visualization logic as seen in FIG. 6.
Figure 8:
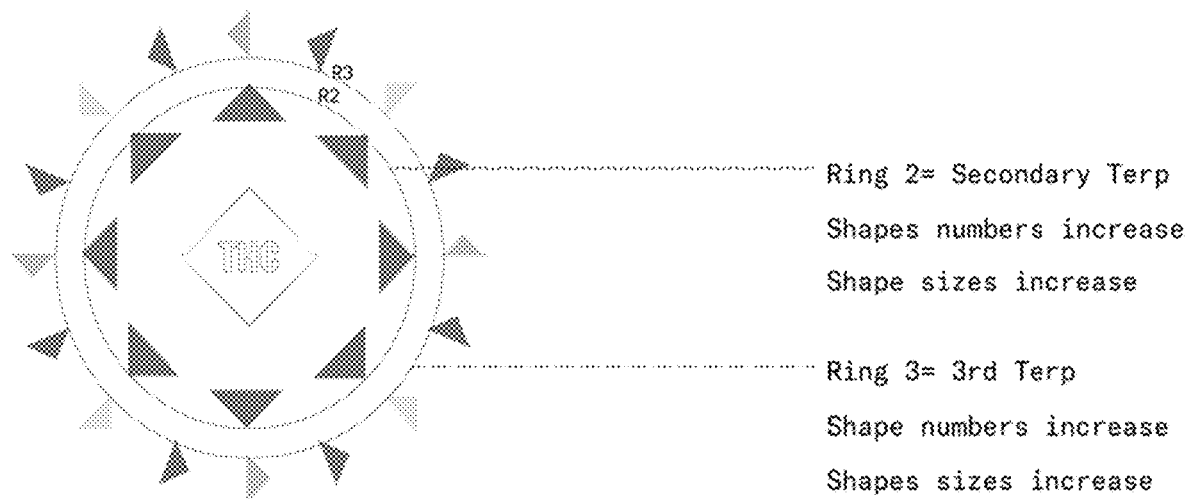
FIG. 8 is an alternate further detailed visualization logic as seen in FIG. 6.
Figure 9:
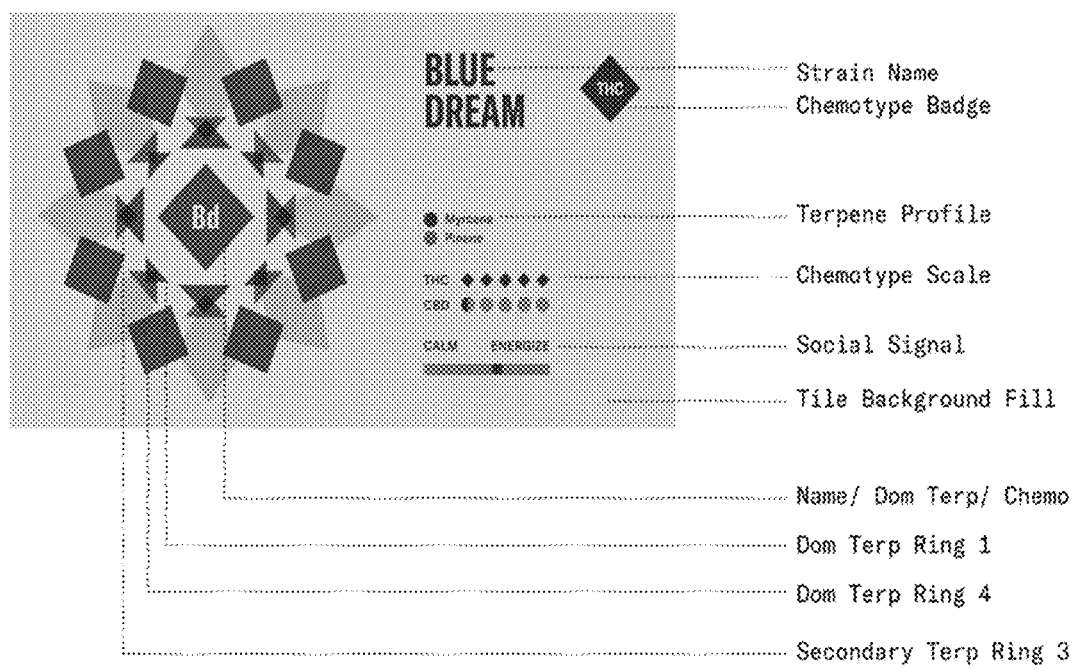
FIG. 9 is a further detailed visualization logic as seen in FIG. 7.

As seen in FIG. 6, the preferred visualization logic used to create visual representations for individual products (a specific producer-processors product) or "strains" (composed of data aggregated across product lines sharing the same lab) is as follows: first, the highest level grouping for a *Cannabis* product (e.g., THC-dominant, CBD-dominant, or Balanced) is provided, and can be represented by central shape 500. As seen in FIG. 5, this shape is located at the center of the visualization, and in the example provided, the highest level grouping of the *Cannabis* product is identified as THC-dominant. Next, additional rings (e.g., R1, R2, R3, R4, etc.) can be added to the central shape 500, with the number of additional rings preferably determined by the total number of "significant" terpenes for that product. Once the number of significant terpenes are identified and additional rings are added to the visualization logic, additional shapes (e.g., S1, T1, etc.) can be populated along these rings, as seen in FIGS. 7-9. The shapes S1, T1 themselves can represent different types of features of the highest level grouping of the product seen in the central shape 500. For example, rectangular shapes with sharp edges and rounded shapes can represent THC and CBD content of the product, respectively. The colors of the shapes can be dictated by major terpenes present in the product.

The example visualization logic seen in FIGS. 7 and 8 are complementary, with FIG. 7 highlighting rings R1 and R4, while FIG. 8 highlights rings R2 and R3 of the same visualization logic. In the visualization logic, rings R1 and R4 preferably both encode information about the dominant terpene, which also dictates the dominant+background color of each visual. Rings R2 and R3 preferably encode information about secondary and tertiary terpenes, where applicable. Therefore, like the example visualization logic set forth in FIGS. 7 and 8, all visualization logics for product characterizations and recommendations preferably comprise rings designating dominant terpenes, with optional additional rings representing additional secondary and/or tertiary (etc.) terpenes.

Further, in the visualization logic seen in the Figures, shape size and color are related to the levels of a given terpene. More specifically, the length and width of the shapes surrounding the central shape are preferably determined by THC and CBD levels. In the example visualization logic set forth in FIGS. 5-9, higher THC or CBD levels result is more elongated rectangular or oval shapes, respectively. For example, a product with very high THC levels will have long, thin rectangular shapes that appear "pointy," whereas a product with low THC levels will contain rectangular shapes that appear less elongated and more square. Products containing THC and little or no CBD contain only rectangular shapes, products with CBD and little or no THC contain only rounded shapes, and products with a mixture of THC and CBD contain both kinds of shapes. Each shape can be either a full or half shape (e.g. full square vs. a half square). The fullness and total number of shapes is determined the levels of that products major terpenes. Of course, alternative visualization logic sets can be used in accordance with a system or user preference.

As seen in the example of FIG. 9, the color-coding of each visualization is based on that products terpene profile, with the primary color determined by the "dominant" terpene, i.e. the terpene present and the highest levels. In this example visualization logic, each of the major terpenes is represented by a unique color, and each product represented by a visualization logic contains a subset of these colors based on its particular composition.

Figure 10:
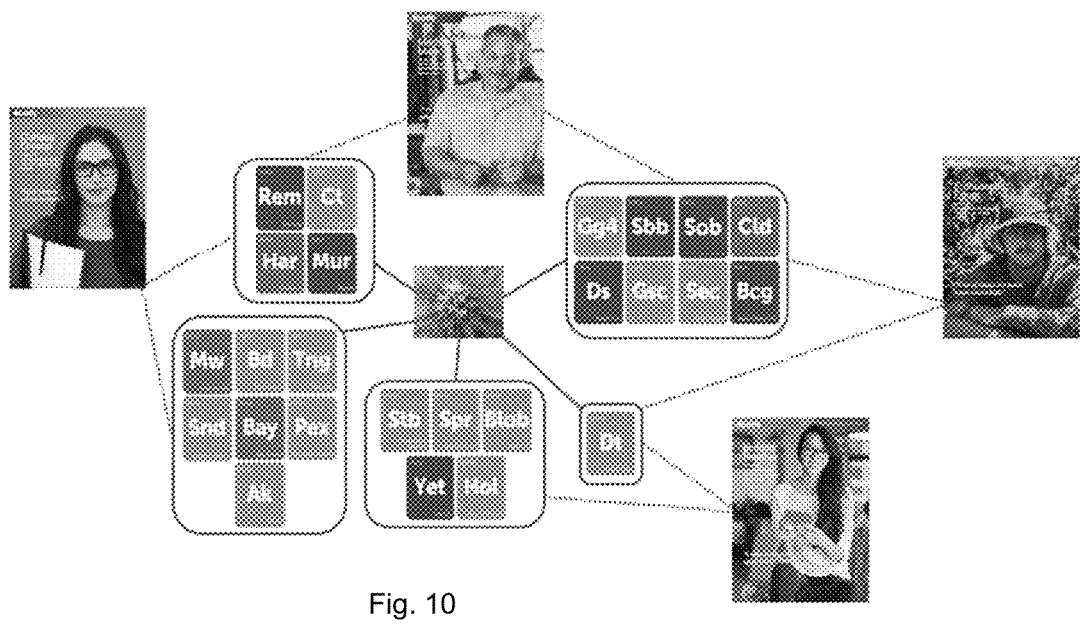
FIG. 10 is sample user-specific output of the recommendation system of the present invention.

This hierarchical system of organization and visualization, based on objective lab data measurements of the composition of *Cannabis* products, also serves as the basis of recommendation system. In response to simple user inputs (e.g. questions about their desired psychoactive effects), users can be recommended to try products within distinct groupings in the hierarchy. An example of the manner in which products are recommended to users based the classification model can be seen in FIG. 10.

Generally, the methods and apparatus (also referred to as a "recommendation system") receive input from a potential purchaser (i.e., a "user"). The user input includes user data which includes, for example, user preferences such as taste, level of psychoactive effects, and the like. Other user data may include demographic values, such as age, sex, or experience level consuming *Cannabis* products.

The recommendation system may be configured with a database or library that contains product information. The product information is descriptive of the regulated products in ways that will provide for correlation with the user data and improve fulfillment. Generally, the correlation of user data and product information is according to algorithms implemented by the recommendation system, thus enabling selection of products that closely correlate to customer requests.

Prior to discussing the technology disclosed herein in detail, aspects of some terms are now introduced.

As discussed herein, the term "user account" generally refers to an account maintained on behalf of a user to facilitate at least one of tracking of user data, selection and order of a regulated product. As discussed herein, the term "merchant account" generally refers to an account maintained on behalf of a merchant to facilitate evaluation of merchant operations, such as sales operations, orders placed with suppliers, inventory and other related information for user selection and acquisition of the selected regulated product.

As discussed herein, the term "merchant" as well as "online store" and "website" are related. These terms generally refer to offerings by another (the merchant) accessible through a network, such as through browser over the Internet. As discussed herein, the merchant offers goods and/or services for sale to shoppers (which are also referred to herein as "users" of the user application).

Referring now to FIG. 1, an exemplary embodiment of a recommendation system 100 is shown. In this example, the recommendation system 100 permits a user making use of a user device 110 to securely, rapidly and automatically complete a purchase transaction. In this example, each user device 110 shares a common user account 105. The user account 105 provides for convenient storing and sharing of information between user devices 110.

Exemplary user devices 110 as may be used in the recommendation system 100 include, without limitation, a personal computer (PC) 111, a laptop 112, a tablet computer 113, a smartphone 114, and a biometric monitor 115. Generally, each user device 110 includes a display 120. Each of the display 120 offer the user a visual interface for interaction with the recommendation system 100. For example, the recommendation system 100 may be presented as a browser interface that makes use of known techniques for user interaction.

Generally, each user device 110 is in communication with network 150 through communications channel 160. The network 150 is also in communication with merchant server 181 and may further communicate with a supplier server 182. In this example, merchant server 181 contains instruction sets governing merchant operations and serves a plurality of user accounts 105. Supplier server 182 may be an e-commerce system server generally configured for transactions between suppliers (wholesalers) and merchants (retailers) and further, the supplier server 182 may contain product information beyond that which is supplied to the merchant. The foregoing are merely illustrative of the architecture of the recommendation system 100 and is not meant to be limiting.

In this example, any user device 110 may include conventional software such as productivity tools (e.g., word processing, spreadsheets, etc.) and at least one browser. Tablet computer 113 or smartphone 114 may also include at least one "app" (defined generally as a purpose oriented application that may include network communications as part of the functionality), as well as a biometric sensor 124 that can be a conventional optical scanner configured with an appropriate app for use as a fingerprint reader. The fingerprint reader may include software for receiving data from the scanner and interpreting the data within the context of a fingerprint. Other user devices 110 may include a biometric sensor 124 and/or other equipment useful for implementing authentication schemes. Thus, the recommendation system may further implement security measures for securing access to the user device 110.

The biometric device 115 may be a personal fitness device or another specialized device. Generally, the biometric device 115 collects and provides personal data. The personal data may be provided to another one of the user devices 110 or directly to the merchant system 181. Personal data that may be collected by the biometric device 115 includes, for example, heart rate, body temperature, blood pressure and other such parameters. The personal data may be communicated to other components of the recommendation system 100.

Once a user new to the recommendation system 100 has established the user account 105, the user may then enter the user data including at least one of user preferences, financial information and user physiology data for storage in the user account 105. Data entry into the user account 105 may be performed manually and/or electronically. Electronic data entry may include, for example, electronic entry of baseline personal data for use as a control or for comparison sake to collected user input data. The baseline personal data for the user may include physiological parameters collected in a normal, resting state for the user.

Once the user has established the user account 105, the user may login to the product categorization and visualization system, which the recommendation system is built upon, and at any time search for offerings of a merchant for a specific regulated product, or may view offers of regulated products from respective merchants. The user may enter preference data or experience data to select a specific product and determine a merchant offering the same. Alternatively, where the user is unfamiliar with the regulated products or may not have any preference data or experience data for input, the recommendation system may make recommendations based on the user data.

For example, in the case of *Cannabis*, the user may be presented with a series of questions by the recommendation system that support a decision tree. Examples of questions for the user include:

| Question | Answer |
| --- | --- |
| Do you want to avoid getting high? | Y/N |
| Do you want to experience psychoactive effects but are nervous/sensitive/lightweight | Y/N |
| Do you definitely want to get high? | Y/N |
| Do you want psychoactive effects but are worried about certain side-effects, e.g. anxiety or hunger. | Y/N |
| Have you tried a specific product before? | Y/N |
| Are you interested in a product for pure recreational purposes or also for medicinal use? | Y/N |
| Do you have a preference for a particular form of product, such as natural form, cooking additive, oil, capsule/pill form, candy or beverage? If so, check any applicable form from those listed below. | Y/N |
| Natural form | € |
| Cooking additive | € |
| Capsule or pill | € |
| Candy | € |
| Beverage | € |
| Prepared foods | € |
| Other | € |

Figure 2:
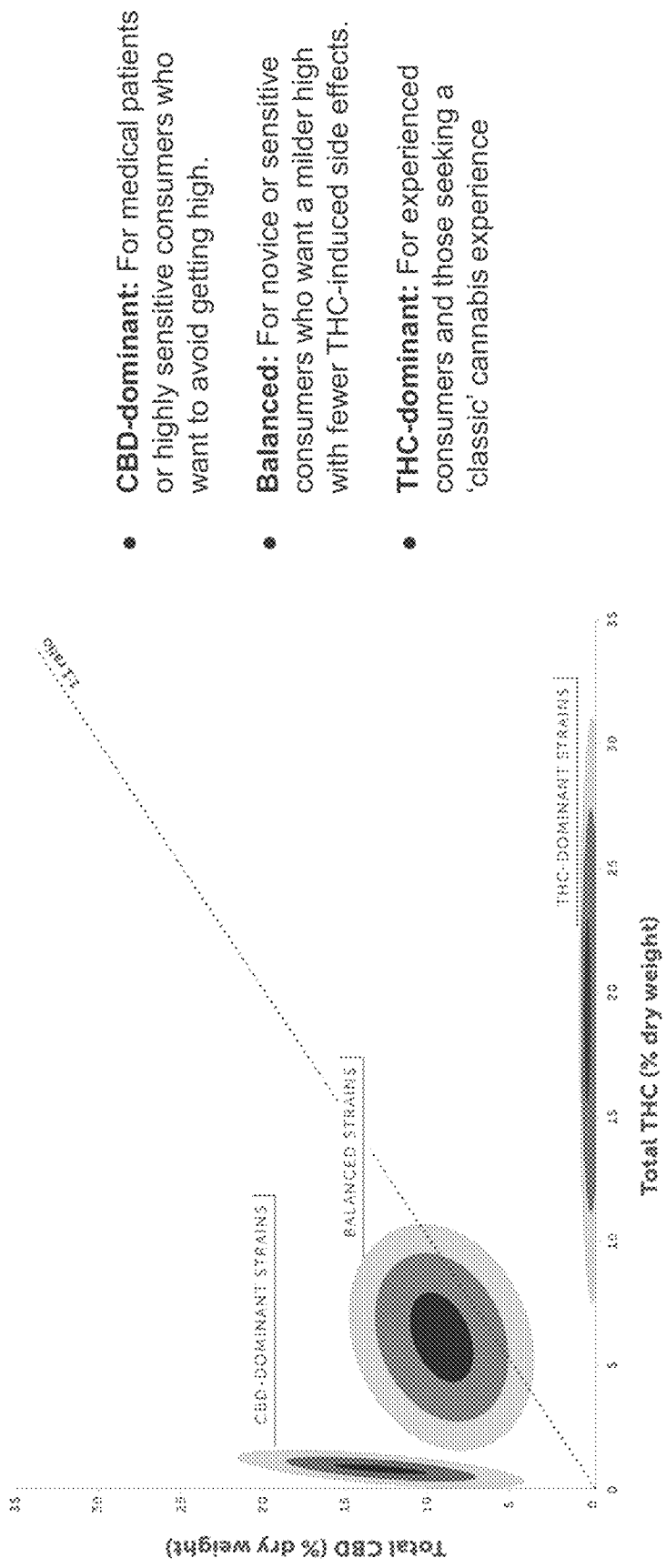
FIG. 2 is a graphic depicting distributions of products according to content.

At this level of decision tree, the recommendation system begins to bias selection of *Cannabis* products based on content of the various psychoactive substances either at relatively high levels of the organization hierarchy (i.e., strains that are THC-dominant, CBD-dominant, or Balanced THC/CBD) or at lower levels (i.e. terpene groupings) and the effects that they provide to users. Reference may be had to FIG. 2 which depicts distributions of *Cannabis* products according to content.

At the next level down in the decision tree, the user may be asked additional questions that further sub-categorize products within a general product category, such as whether there are specific flavors they prefer, whether they want strains that are better for certain issues, and others. Both levels and the batch-specific level could be further personalized with more specific recommendations with relevant user feedback, either based on population-level data (if user is brand new) or at the individual level (if a user has provided us with enough feedback historically).

In FIG. 2, the shaded areas depict a population of data points, with each data point representing total content of CBD and THC for a particular strain of *Cannabis*. Darker areas indicate a greater prevalence of strains.

The CBD-dominant strains may be preferred by medical patients or highly sensitive consumers who want to avoid getting high. THC-dominant strains may be preferred by experienced consumers and those seeking a "classic" *Cannabis* experience. Balanced strains may be preferred by novice or sensitive consumers who want a milder high with fewer THC-induced side effects.

The selection process may continue with questions such as: are there specific flavors you prefer? Do you want strains that may be better or worse for [certain things], which could include anxiety, inflammation or pain, relaxation, sleepiness, or if the user has a cost limit?

The recommendation system 100 may be further personalized with more specific recommendations with relevant user feedback, either based on population-level data (if user is brand new) or at the individual level (if a user has provided prior historical feedback).

Once the selection process has received the requested preference information, the recommendation system 100 will make recommendations to the user. The recommendations may include identity of a particular strain of *Cannabis*, a recommended quantity for ingestion, recommended techniques for ingestion, and other such aspects.

The recommendations may be based upon a variety of factors. For example, the recommendation system 100 may provide each user with a specific user experience feedback facility. The user experience feedback facility may query the user for a variety of parameters. Questions may solicit information regarding, for example, a degree of euphoria, hunger, queasiness, relaxation and other such subjective aspects. Other input to the user experience feedback facility may include objective data such as personal data collected by the biometric device 115.

The user experience feedback may result in refined personal recommendations for future purchasing. In some embodiments, user experience feedback is aggregated. Aggregated user experience feedback may be used to develop and refine a heuristic algorithm for making recommendations to new users or users with changed input data.

Figure 3:
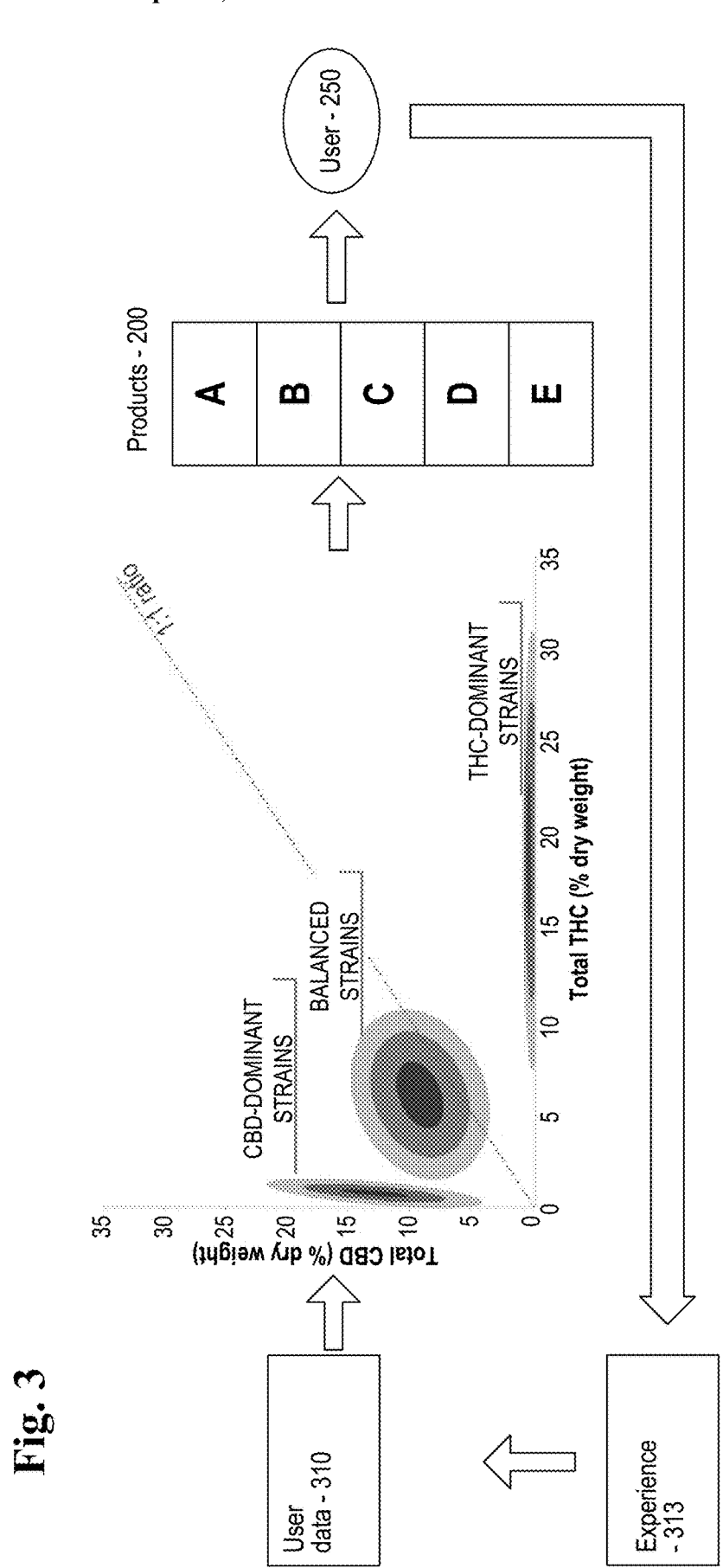
FIG. 3 is a flow chart providing an exemplary process for generating recommendations using the recommendation system disclosed herein.

FIG. 3 is a process diagram depicting one aspect of user input and ongoing updating of the recommendation system. In FIG. 3, the user initiates a request for a recommendation. User data 310, such as preference data 312 and/or personal data 311, are input into the recommendation system 100. When considering the inputted user data and aspect of CBD and THC content related to the products which fall within the classification of the user's preference data 312, the recommendation system 100 makes reference to the appropriate data set, such as that set forth in FIG. 2, to identify the target on the grid as to a product or products falling within recommended THC-CBD content percentages. From the user data 310 and the content information (FIG. 2), the recommendation system 100 narrows the pool of products 200 for recommendation to a limited set. In this illustration, the candidate products 200 for recommendation are denoted as A, B, C, D and E. Of course, the CBD and THC content are merely one aspect or parameter considered by the recommendation system 100. Consideration of the various other salient parameters may result in recommendation of fewer candidate products 200. Once selected, the user 250 will indulge and have an experience 313. The experience data is tracked and used to assist with future recommendations.

If, however, a user does not agree with the recommendations of products 200 provided by the recommendation system 100, the user can provide feedback of experience data 313 or additional preference data 312 to alter and update the recommendation. For example, the user may indicate that the recommended products 200 contain either too much or too little THC, too much or too little CBD, will cause an effect that differs from the user's preference, etc. Based on this feedback, the recommendation system 100 can update the user data 310 and re-assess the totality of the inputted information to update, in real time, a revised set of recommended products 200. This is process is set forth with further detail in FIG. 4.

Figure 4:
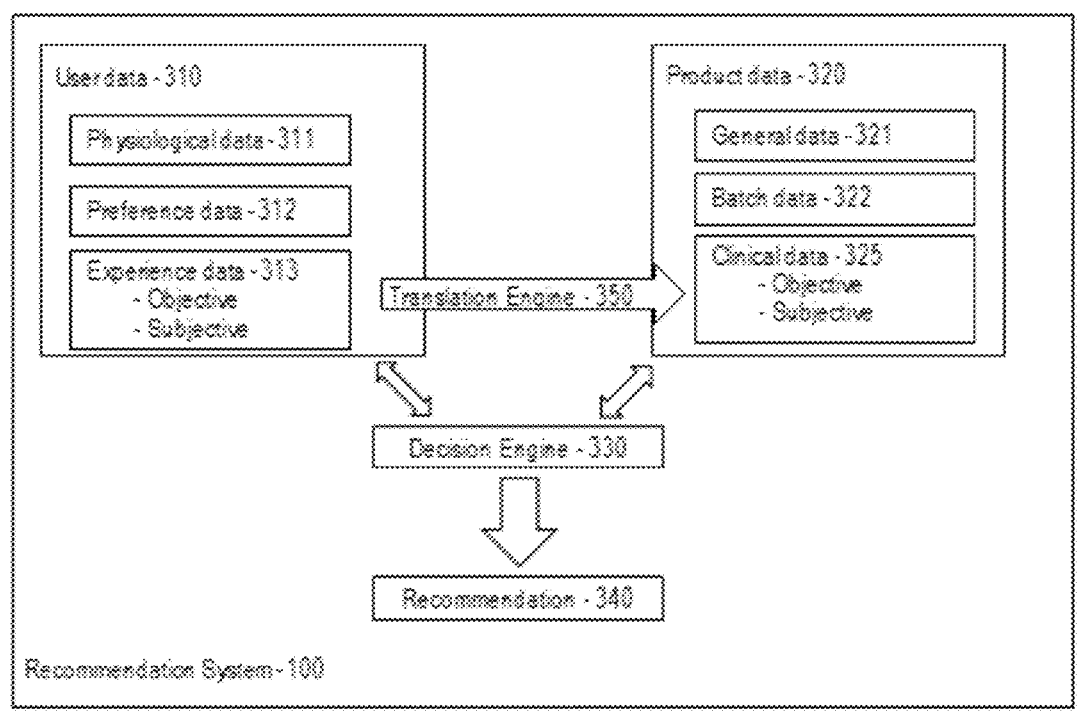
FIG. 4 is a schematic diagram providing an overview of a system for recommending products.

FIG. 4 is a block diagram depicting aspects of the recommendation system and is useful for describing an exemplary embodiment of a process for making a recommendation of regulated product.

As shown in FIG. 4, user data 310 and product data 320 are provided as inputs to a decision engine 330. In this example, the user data 310 includes baseline personal data 311, preference data 312, and experience data 313. Generally, the baseline personal data 311 includes objective aspects such as, without limitation, age, sex, race, weight, heart rate, blood pressure, and the like. The user preference data 312 may include information related to the type of experience sought and the subjective view of the user as it relates to specific products or product effects. The preference data 312 may be entered contemporaneously, and may be stored with default values suited for the particular user. Generally, the experience data 313, which may be collected during the user experience, is descriptive of the user experience and therefore may be used to develop a degree of conformity to the product description. The experience data 313 may include a subjective component collected from user assessments and reviews, and may also include an objective component, such as updated personal data 311 of the user when under the influence. Examples of personal data that may be monitored while under the influence include aspects such as heart rate, blood pressure, thirst, food intake, and the like.

Generally, the product data 320 includes general data 321, batch data 322, and clinical data 325. The general data 321 generally includes aspects such as name, supplier identity, and fundamental aspects such as average content, density, storage recommendations, manner of consumption, and the like. The batch data 322 may include more specifics, including actual test results from a laboratory or scientific research on a given product. The clinical data 325 may include objective data, such as that derived from administration in a controlled setting where physiological parameters are monitored, and may include subjective data, such as user feedback. The clinical data 325 may be derived from the experience data 313 of multiple users, taking into account variations between batches, user physiology, and the like. Stated another way, the clinical data 325 may be experience data 313 that is normalized over a statistically significant population using aspects such as the baseline personal data 311, and therefore predictive of a user experience for a new user.

Generally, the recommendation system 100 will task the decision engine 330 with the task of making a recommendation 340 for a particular user. That is, for each user, given a set of respective baseline personal data 311, preference data 312, and experience data 313, the decision engine 330 may apply a heuristic algorithm that derives recommendations 340 from other sets of baseline personal data 311 maintained in the recommendation system 100. Generally, the recommendations 340 are arrived at by using large data sets to improve correlation between the expressed preferences 312 and the experience 313, combined and compared with general data 321, batch data 322, and clinical data 325 regarding each potential product for recommendation.

The recommendation system 100 may also include a translation engine 350. Generally, the translation engine 350 weights user experience data 313 according to the personal data 311 to provide for additions to the clinical data 325. In some embodiments, translation (or correlation) is performed by the decision engine 330 during processing.

As one may surmise, the iterative processing of large data sets with diverse data lends itself well to use of artificial intelligence. Accordingly, the decision engine 330 may implement artificial intelligence. The artificial intelligence may be provided as a neural network, for example. In one embodiment, the neural network makes use of the user preferences 312 as the input layer, and applies aspects such as the baseline personal data 311 and batch data 322 in the hidden layers, and then may continuously update the information stored and reviewed for possible recommendation 340 based on changes to the user preference data 312 or user experience data 313, or updated information to product clinical data 325. The artificial intelligence may also continue to understand the baseline personal data 311 for desired effect of the regulated product, and understand how it compares to the objective clinical data 325 of numerous users, with the both the user data 310 and the product data 320 able to update in real time.

The recommendation system 100 may also aid in the procurement process. That is, for at least one product recommendation, the recommendation system 100 may then query the respective merchant servers 181 (and/or supplier servers 182) to identify availability of the recommended product and location for pick-up of the same, which recommendation may be made by assessing a geolocation of a user. Once sources (i.e., merchants) for the recommended product have been identified, any regulatory constraints on a transaction can be identified and may be used to qualify availability and recommendations. For example, if a prescription or medical use license is required by a state where pick-up of inventory for the recommended product may be available, then the user may be alerted to the requirement. Alternatively, the recommendation system 100 may qualify users and conceal the availability of the recommended product or particular locations for pick-up from users that are disqualified from purchase on the basis of a respective user profile, as discussed below.

Limitations on procurement may be specific to each of the products, and therefore may be tracked in the recommendation system 100 as a part of the product data 320. Some limitations on procurement may be specific to external factors, such as jurisdictions laws or regulations. For example, one jurisdiction may require early closing of dispensaries while a neighboring jurisdiction permits extended hours of operation. A variety of potentially regulated parameters may be tracked by the recommendation system 100, all of which may factor into the recommended products 200. Examples of external factors that may govern transactions under applicable laws or regulations include, without limitation: state laws, hours of operation, merchant licensing, sales limitations, user age, prescription requirements, use licensing, residential information, user restrictions, user prohibitions, criminal records, credit, and other such factors.

Accordingly, the recommendation system 100 may include a regulatory database. The regulatory database may be in communication with other regulatory tracking services, such as LEXIS or WESTLAW. As the regulatory database may be accessed during the process of recommendation generation and maintained up-to-date, the recommendation system 100 may aid merchants and users with regulatory compliance, which may also affect the recommendations made by recommendation system 100 to fulfill or comply with applicable laws or regulations in the regulatory database. This will ensure that any recommendation for a regulated product made by the recommendation system 100 is ideally in accordance with applicable laws.

Taken together, the recommendation system 100 can identify one or more recommended products 200 based on input of any one or more of objective lab testing data, subjective user preference data, product data 320, geolocation of a user, and regulatory, legal, or other limitations regarding locations at which recommended products 200 may be provided. Therefore, the recommended products 200 will be ones which (1) the user can conveniently and legally pick up, (2) are available for purchase with sufficient inventory at identified merchants 181, (3) match the user's preferences for manner of consumption, graphical indication of THC-CBD content (as seen in FIG. 2), (4) match the user's subjective preferred experience, and (5) fit the user's objective personal data to confirm appropriate and advisable levels of recommended consumption.

Having introduced aspects of the recommendation system for making recommendations, selections and purchasing of regulated products, some additional features and aspects are now introduced.

Advantageously, the recommendation system disclosed herein provides for recommendations that correlate well with user preferences. That is, for example, by implementation of a public system, a large set of user data and product data is attainable. This large data set, in combination with sophisticated algorithms such as a neural network, provides for recommendations with a degree of sophistication that is not attainable by a salesperson, medical practitioner, or other such individual. Further, such recommendations may be made with complete privacy, at any time of day. By employing the recommendation system with a regulation database, regulatory compliance may be assured, thus removing the responsibility for compliance assurance from sales staff, thus enhancing sales.

The recommendation system may be provided as a set of machine executable instructions on non-transitory machine readable media. Generally, each user device is configured to store machine executable instructions on non-transitory machine readable media (such as in read-only memory (ROM), random-access-memory (RAM), or in a non-volatile storage unit such as a hard disk, solid state drive, or the equivalent). The machine executable instructions may be referred to herein as "software," as an "application," as a "client," a "process," a "plug-in," an "add-in," an "add-on," an "extension," and by other similar terms. The machine executable instructions generally provide for functionality through operation of various methods as may be presented herein as well as others that may be apparent to those skilled in the art.

Some of the machine executable instructions stored on non-transitory machine readable media may include an operating environment also referred to as an operating system. For example, and as presented herein, a suitable operating environment is WINDOWS (available from Microsoft Corporation of Redmond Washington). Other operating environments include iOS from Apple of Cupertino California and ANDROID available from Alphabet of Mountain View California Software as provided herein may be developed in, for example, SQL language, which is a cross-vendor query language for managing relational databases. Aspects of the software may be implemented with other software. For example, user interfaces may be provided in XML, HTML, a variety of scripting languages and the like.

More specifically, given the highly configurable nature of computing systems, the terms "computer" and "user device" as well as other similar terms are to be construed to include any configuration of components and/or software as needed to provide for the intended functions as well as extensions thereof. The architecture of the recommendation system may be modified as deemed appropriate for implementation.

The recommendation system may be implemented over a network, such as the Internet.

The biometric device may be a commercially available device, such as a FITBIT personal electronic device, an APPLE WATCH personal electronic device, or any other similar type of device. The biometric device may be a specialized device configured for operation with the recommendation system. The biometric device may include additional functionality. For example, the biometric device may provide user alerts, a screen or other user interface to facilitate user interaction with the recommendation system or other such functionality.

The recommendation system may implement self-training algorithms such as artificial intelligence. For example, the recommendation system may implement a neural network. The neural network may accept, for example, personal data to correlate observed physiological effects of products with the physiology of the user. The correlation may be for the individual user, a segment of the user population, or the user population as a whole.

Supplier data, which may be useful for formulating recommendations, may include without limitation, density, chemical composition, such as from laboratory analyses of regulated products, vintage, source, certification by an appropriate standard, a set of user experience feedback, reviews and any other data deemed appropriate. The supplier data may be input through a standardized interface for communication between suppliers and merchants.

The recommendation system may implement user security, privileges, certificates, and other techniques to ensure integrity of the process and authenticity of the regulated products delivered to the user. The recommendation system may be operated with regard for privacy laws, such as HIPAA (i.e., the "Health Insurance Portability and Accountability Act") which sets forth requirements for control of medically sensitive information.

The recommendation system may include advertising. The recommendation system may be used to sell other items such as related paraphernalia. The recommendation system may be configured for facilitating routine or automatic ordering.

Various other components may be included and called upon for providing for aspects of the teachings herein. For example, additional materials, combinations of materials and/or omission of materials may be used to provide for added embodiments that are within the scope of the teachings herein.

Any readers of any patent issued on this application should note that Applicants do not intend any of the appended claims or claim elements to invoke means-plus-function terminology as related to 35 U.S.C. section 112(f) unless the words "means for" or "step for" are explicitly used in the particular claim.

When introducing elements of the present invention or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A recommendation system for normalizing subjective components across different users in recommending regulated products for consumption, the system comprising:
   a user interface for receiving user input from one or more user devices, the user input including (1) physiological data representative of health-monitor data from a wearable user device that represents real-time physiological condition of a user and (2) preference data for the user; and
   a decision engine configured to make a recommendation of a matching product for the user based on applying a machine learning model to the user input, wherein:
   the machine learning model corresponds to a combination of experience data corresponding to and normalized across multiple clinical subjects and multiple different batches of available products, wherein the experience data is weighted and correlated according to physiological information associated with the clinical subjects,
   applying the machine learning model includes:
      providing the user preference as an input,
      predicting a user experience for the user based on applying one or more weights according to the physiological data of the user, the user preference, and the machine learning model, and
      identifying in real-time the matching product that corresponds to a combination of the one or more weights and the user preference;
   wherein the user interface is for communicating the recommendation for the matching product to the user.

2. The recommendation system of claim 1, wherein:
   the physiological data for the user and/or for each of the clinical subjects includes age, sex, race, weight, heart rate, blood pressure, or a combination thereof;
   the experience data includes subjective descriptions of the clinical subjects regarding the available products; and
   applying the machine learning model corresponds to
      normalizing the subjective descriptions of the clinical subjects and the preference data of the user according to corresponding instances of the physiological data; and
      identifying the matching product based on comparing the normalized descriptions and the normalized preference data.

3. The recommendation system of claim 2, wherein applying the machine learning model corresponds to:
   normalizing the subjective descriptions based on correlations between data corresponding to the user and the clinical subjects;
   predicting experiences for the user consuming one or more of the multiple available products based on the correlations; and
   identifying the matching product having a predicted experience closest to the preference data of the user.

4. The recommendation system of claim 1, wherein:
   the machine learning model corresponds to correlations between the physiological data, objective experience data, and subjective experience data,
      the objective experience data including heart rate, blood pressure, thirst measure, food intake data, or a combination thereof collected based on monitoring the clinical subjects while under the influence of corresponding available products, and
      the subjective experience data including user feedback, and
      the correlations representative of effects of corresponding products on the clinical subjects that accounts for the physiology of the clinical subjects; and
   applying the machine learning model corresponds to comparing the preference data and the physiological data of the user to the subjective experience data of the clinical subjects according to the correlations.

5. The recommendation system as in claim 1, wherein:
   the user interface is for receiving feedback from the user regarding experiences from consuming the matching product; and
   further comprising:
   a translation engine for adjusting the received user experiences according to the physiological data, wherein the adjusted result is combined with clinical data used to further train the machine learning model.

6. The recommendation system of claim 1, further includes:
   a merchant interface for receiving merchant input, the merchant input including product information descriptive of the available products, wherein the available products are *Cannabis* products having levels of THC and CBD along with one or more terpenes; and
   wherein
   identifying the matching product includes
      identifying a group of products from within the available products according to the levels of THC and CBD; and
      identifying the recommended product from the identified group of products according to the one or more terpenes.

7. The recommendation system as in claim 1, further comprising:
   a visual design logic configured to generate a visual label representative of the matching product, wherein the visual label uses a shape, a color, a location of the shape and/or color, an arrangement thereof, or a combination thereof to communicate characteristic traits of the individual product to the user; and
   wherein
   the user interface is for communicating the visual label for the recommendation.

8. The recommendation system as in claim 7, wherein the visual label includes (1) a center portion that represents levels of THC and CBD for the matching product and (2) one or more surrounding portions arranged around the center portion and represent one or more terpenes of the matching product.

9. A non-transitory machine-readable media having stored thereon machine-executable instructions that, when executed by one or more processors, performs a method for normalizing subjective components across different users in recommending regulated products for consumption, the method comprising:

receiving user input from one or more user devices, the user input including (1) physiological data representative of health-monitor data from a wearable user device that represents real-time physiological condition of a user and (2) preference data for the user;

generating a recommendation of a matching product for the user based on applying a machine learning model to the user input, wherein the machine learning model corresponds to a combination of experience data corresponding to and normalized across multiple clinical subjects and multiple different batches of available products, wherein the experience data is weighted and correlated according to physiological information associated with the clinical subjects, applying the machine learning model includes
providing the user preference as an input,
predicting a user experience for the user based on applying one or more weights according to the physiological data of the user, the user preference, and the machine learning model, and
identifying in real-time the matching product that corresponds to a combination of the one or more weights and the user preference.

10. The non-transitory machine-readable media of claim 9, wherein:

the physiological data for the user and/or for each of the clinical subjects includes age, sex, race, weight, heart rate, blood pressure, or a combination thereof;

the experience data includes subjective descriptions of the clinical subjects regarding the available products; and applying the machine learning model corresponds to
normalizing the subjective descriptions of the clinical subjects and the preference data of the user according to corresponding instances of the physiological data; and
identifying the matching product based on comparing the normalized descriptions and the normalized preference data.

11. The non-transitory machine-readable media of claim 10, wherein applying the machine learning model corresponds to:

Normalizing the subjective descriptions based on correlations between data corresponding to the user and the clinical subjects;

predicting experiences for the user consuming one or more of the multiple available products based on the correlations; and identifying the matching product having a predicted experience closest to the preference data of the user.

12. The non-transitory machine-readable media of claim 9, wherein:

the machine learning model corresponds to correlations between the physiological data, objective experience data, and subjective experience data, the objective experience data including heart rate, blood pressure, thirst measure, food intake data, or a combination thereof collected based on monitoring the clinical subjects while under the influence of corresponding available products, and the subjective experience data including user feedback, and the correlations representative of effects of corresponding products on the clinical subjects that accounts for the physiology of the clinical subjects; and applying the machine learning model corresponds to comparing the preference data and the physiological data of the user to the subjective experience data of the clinical subjects according to the correlations.

13. The non-transitory machine-readable media of claim 9, wherein the machine-executable instructions correspond to the method that further comprises:

receiving feedback from the user regarding experiences from consuming the matching product; and adjusting the received user experiences according to the physiological data, wherein the adjusted result is combined with clinical data used to further train the machine learning model.

14. The non-transitory machine-readable media of claim 9, wherein the machine-executable instructions correspond to the method that further comprises:

receiving merchant input including product information descriptive of the available products, wherein the available products are *Cannabis* products having levels of THC and CBD along with one or more terpenes; and wherein identifying the matching product includes
identifying a group of products from within the available products according to the levels of THC and CBD; and
identifying the recommended product from the identified group of products according to the one or more terpenes.

* * * * *